US007012157B2

(12) United States Patent
Borgmeier et al.

(10) Patent No.: US 7,012,157 B2
(45) Date of Patent: Mar. 14, 2006

(54) PREPARATION OF (METH)ACRYLIC ACID

(75) Inventors: Frieder Borgmeier, Mannheim (DE); Frank Rosowski, Mannheim (DE); Hans Martan, Frankenthal (DE); Klaus Joachim Müller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/934,624

(22) Filed: Sep. 7, 2004

(65) Prior Publication Data

US 2005/0065372 A1    Mar. 24, 2005

Related U.S. Application Data

(60) Provisional application No. 60/504,959, filed on Sep. 23, 2003.

(30) Foreign Application Priority Data

Sep. 23, 2003   (DE) ................................ 103 44 265

(51) Int. Cl.
    *C07C 51/16*        (2006.01)
(52) U.S. Cl. .................................... 562/547
(58) Field of Classification Search ............... None
    See application file for complete search history.

(56) References Cited

U.S. PATENT DOCUMENTS

| 4,297,247 | A | 10/1981 | Krabetz et al. |
| 5,677,261 | A | 10/1997 | Tenten et al. |
| 5,739,391 | A | 4/1998 | Ruppel et al. |
| 5,821,390 | A | 10/1998 | Ruppel et al. |
| 5,910,608 | A | 6/1999 | Tenten et al. |
| 6,036,880 | A | 3/2000 | Komada et al. |
| 6,063,728 | A | 5/2000 | Hinago et al. |
| 6,143,916 | A | 11/2000 | Hinago et al. |
| 6,169,214 | B1 | 1/2001 | Tenten et al. |
| 6,294,685 | B1 | 9/2001 | Ushikubo et al. |
| 6,395,936 | B1 | 5/2002 | Arnold et al. |
| 6,610,629 | B1 | 8/2003 | Hinago et al. |
| 2003/0017944 | A1 | 1/2003 | Hinago et al. |
| 2003/0088124 | A1 | 5/2003 | Dubois |
| 2003/0187298 | A1 | 10/2003 | Borgmeier et al. |
| 2004/0054222 | A1 * | 3/2004 | Felder et al. ............... 562/547 |
| 2004/0063988 | A1 | 4/2004 | Hechler et al. |
| 2004/0082810 | A1 | 4/2004 | Borgmeier et al. |
| 2004/0097368 | A1 | 5/2004 | Borgmeier et al. |
| 2004/0102648 | A1 | 5/2004 | Borgmeier et al. |
| 2004/0138500 | A1 | 7/2004 | Borgmeier |
| 2004/0192965 | A1 | 9/2004 | Petzoldt et al. |
| 2004/0204607 | A1 | 10/2004 | Machhammer et al. |
| 2004/0242926 | A1 | 12/2004 | Dieterle et al. |

FOREIGN PATENT DOCUMENTS

| DE | 29 09 671 | 10/1980 |
| DE | 44 31 957 | 3/1995 |
| DE | 44 42 346 | 5/1996 |
| DE | 198 35 247 | 2/1999 |
| DE | 199 10 506 | 9/2000 |
| DE | 100 29 338 | 1/2002 |
| DE | 100 46 672 | 3/2002 |
| DE | 100 51 419 | 4/2002 |
| DE | 101 22 027 | 5/2002 |
| DE | 101 01 695 | 7/2002 |
| DE | 101 18 814 | 10/2002 |
| DE | 101 19 933 | 10/2002 |
| DE | 102 54 278 | 2/2004 |
| DE | 102 46 119 | 4/2004 |
| DE | 102 54 279 | 6/2004 |
| DE | 103 13 208 | 10/2004 |
| DE | 103 13 213 | 10/2004 |
| DE | 103 16 465 | 10/2004 |
| EP | 0 529 853 | 3/1993 |
| EP | 0 603 836 | 6/1994 |
| EP | 0 608 838 | 8/1994 |
| EP | 0 700 893 | 3/1996 |
| EP | 0 895 809 | 2/1999 |
| EP | 0 962 253 | 12/1999 |
| EP | 1 080 784 | 3/2001 |
| EP | 1 090 684 | 4/2001 |
| EP | 1 106 598 | 6/2001 |
| EP | 1 123 738 | 8/2001 |
| EP | 1 192 982 | 4/2002 |
| EP | 1 192 983 | 4/2002 |
| EP | 1 192 986 | 4/2002 |
| EP | 1 192 987 | 4/2002 |
| EP | 1 192 988 | 4/2002 |
| EP | 1 193 240 | 4/2002 |
| EP | 101 45 958 | 5/2002 |
| EP | 1 238 960 | 9/2002 |
| EP | 1 254 706 | 11/2002 |

(Continued)

OTHER PUBLICATIONS

Derwent Publications, JP 2000-256257, Sep. 19, 2000.
Derwent Publications, JP 10-036311, Feb. 10, 1998.
Derwent Publications, JP 11-057479, Mar. 2, 1999.
E. Balcells, et al., "Partial oxidation of propane and propene to acrylic acid over a Mo-V-Te-Nb oxide catalyst", Catalysis Letters, vol. 87, No. 3-4, Apr. 2003, pp. 195-199.

(Continued)

*Primary Examiner*—Paul A. Zucker
(74) *Attorney, Agent, or Firm*—Oblon, Spivak, McClelland, Maier & Neustadt, P.C.

(57) ABSTRACT

A process for preparing (meth)acrylic acid, in which a saturated hydrocarbon precursor compound is conducted through a catalyst charge which consists of two spatially successive catalyst beds I, II in the flow direction of the reaction mixture, each of which contains different catalysts and has different reaction-selectivity behavior.

21 Claims, No Drawings

FOREIGN PATENT DOCUMENTS

| | | |
|---|---|---|
| EP | 1 254 707 | 11/2002 |
| EP | 1 254 709 | 11/2002 |
| WO | WO 99/03825 | 1/1999 |
| WO | WO 00/29106 | 5/2000 |
| WO | WO 02/06199 | 1/2002 |
| WO | WO 02/083615 | 10/2002 |

OTHER PUBLICATIONS

Derwent Publications, JP 07-315842, Dec. 5, 1995.

Kenji Nomiya, et al., "Anderson-Type Heteropolyanions of Molybdenum(VI) and Tungsten(VI)", Polyhedron, vol.6, No. 2, 1987, pp. 213-218.

W. Ueda, et al., "Selective Oxidation of $C_1$-$C_3$ Alkanes over Molybdenum- and Vanadium-based Oxide Catalysts", Kinetics and Catalysis, vol. 40, No. 3, 1999, pp. 401-404.

Derwent Publications, JP 07-232071, Sep. 5, 1995.

Derwent Publications, JP 2000-143244, May 23, 2000.

* cited by examiner

PREPARATION OF (METH)ACRYLIC ACID

The present invention relates to a process for preparing (meth)acrylic acid by heterogeneously catalyzed gas phase partial oxidation of at least one saturated hydrocarbon precursor compound at elevated temperature, by conducting a starting reaction gas mixture which comprises the at least one saturated hydrocarbon precursor compound, molecular oxygen and at least one inert gas and has a starting pressure P through a catalyst charge which is disposed in a reactor unit and whose catalysts are such that their active composition is at least one multimetal oxide M which contains the elements Mo and V, at least one of the elements Te, Sb and Bi, and at least one of the elements from the group consisting of Nb, Ta, W, Ce and Ti, and whose X-ray diffractogram is an X-ray diffractogram which has reflections h, i and k whose peak locations are at the reflections (2Θ) of 22.2±0.5° (h), 27.3±0.50° (i) and 28.2±0.5° (k), the reflection h being the most intense within the X-ray diffractogram and also having a half-height width of at most 0.5° and the half-height width of the reflection i and of the reflection k each being ≦1°.

In this document, the notation (meth)acrylic acid is an abbreviation for methacrylic acid or acrylic acid.

(Meth)acrylic acid forms reactive monomers which are suitable, for example, for preparing polymers which may find use as adhesives, among other uses.

On the industrial scale, one way of preparing (meth)acrylic acid is by heterogeneously catalyzed gas phase partial oxidation of propane or isobutane.

Acrylic acid and methacrylic acid can be obtained in a mixture by heterogeneously catalyzed gas phase partial oxidation of a mixture of propane and isobutane.

Propane and isobutane are therefore referred to in this document as saturated hydrocarbon precursor compounds of (meth)acrylic acid.

Processes for preparing (meth)acrylic acid by heterogeneously catalyzed gas phase partial oxidation of at least one saturated hydrocarbon compound according to the preamble of this document are known (cf., for example, EP-A 1192987, DE-A 10122027, JP-A 2000-256257, EP-A 608838, EP-A 1193240, EP-A 1238960, JP-A 10-36311, EP-A 1254706, DE-A 10051419, EP-A 962253, WO-A 99/003825, JP-A 11-57479 and DE-A 10338529).

A disadvantage of these processes is that the maximum achievable yield of (meth)acrylic acid in single pass of the reaction gas mixture through the catalyst charge (reactor unit) with otherwise predefined process conditions, as a function of the reaction temperature, is not fully satisfactory.

It is an object of the present invention to provide an improved process for preparing (meth)acrylic acid which enables increased yields of (meth)acrylic acid.

We have found that this object is achieved by a process for preparing (meth)acrylic acid by heterogeneously catalyzed gas phase partial oxidation of at least one saturated hydrocarbon precursor compound at elevated temperature, conducting a starting reaction gas mixture which comprises the at least one saturated hydrocarbon precursor compound, molecular oxygen and at least one inert gas and has a starting pressure P through a catalyst charge which is disposed in a reactor unit and whose catalysts are such that their active composition is at least one multimetal oxide M which contains the elements Mo and V, at least one of the elements Te and Sb, and at least one of the elements from the group consisting of Nb, Ta, W, Ce and Ti, and whose X-ray diffractogram is an X-ray diffractogram which has reflections h, i and k whose peak locations are at the reflections (2Θ) of 22.2±0.5° (h), 27.3±0.5° (i) and 28.2±0.5° (k), the reflection h being the most intense within the X-ray diffractogram and also having a half-height width of at most 0.5° and the half-height width of the reflection i and of the reflection k each being ≦1°, wherein the catalyst charge in its entirety consists of two catalyst beds I, II which comprise different catalysts and are spatially successive in the flow direction of the reaction gas mixture, the catalyst bed I being such that if the overall catalyst charge of the same reactor unit were to consist only of catalyst bed of the type I, the selectivity $S^I$ of (meth)acrylic acid formation with otherwise identical conditions of the gas phase partial oxidation would, depending on the conversion, increased by increasing the reaction temperature, of the saturated hydrocarbon precursor compound based on single pass of the reaction gas mixture through the reactor unit, pass through a maximum value $S^I_{max}$, and the catalyst bed II being such that if the overall catalyst charge of the same reactor unit were to consist only of catalyst bed of the type II, the selectivity $S^{II}$ of (meth)acrylic acid formation with otherwise identical conditions of the gas phase partial oxidation would, depending on the conversion, increased by increasing the reaction temperature, of the saturated hydrocarbon precursor compound based on single pass of the reaction gas mixture through the reactor unit, pass through a maximum value $S^{II}_{max}$, with the proviso that the value $S^I_{max}$ is at a lower conversion of the saturated hydrocarbon precursor compound than the value $S^{II}_{max}$ and, with increasing conversion of the saturated hydrocarbon precursor compound, $S^I < S^{II}$, whereas $S^I_{max} > S^{II}_{max}$.

The idea of carrying out the preparation of (meth)acrylic acid by heterogeneously catalyzed gas phase partial oxidation of at least one saturated hydrocarbon compound in a structured catalyst charge is known in abstract form from Catalysis Letters Vol. 87, Nos. 3–4, April 2003, p. 195 to 199. However, a disadvantage of this publication is that it makes no disclosure on the type and manner of the structuring.

Such a structured charge used in EP-A 1193240 is, for example, one which contains only one catalyst, and the volume concentration of this catalyst increases within the charge in the flow direction of the reaction gas mixture.

The background of the present invention is the observation that the selectivity of (meth)acrylic acid formation in a process according to the preamble of this document generally passes through a maximum when, under otherwise constant process conditions, the conversion of the at least one saturated hydrocarbon precursor compound in single pass of the reaction gas mixture through the catalyst charge is increased by increasing the reaction temperature.

In addition, it has been observed that when catalysts having multimetal oxides M as the active composition are prepared in substantially the same way, there are element compositions of the multimetal oxide M which have the characteristic feature that the aforementioned selectivity maximum in the case of catalyst charges having active compositions composed of catalysts having such a multimetal oxide M is at comparatively low conversions of the at least one saturated hydrocarbon precursor compound and is very marked, but decreases markedly with increasing conversion (such element compositions of the multimetal oxide M are referred to hereinbelow as element compositions A), while, in the case of another group of element compositions of the multimetal oxide M (referred to hereinbelow as element compositions B), the corresponding selectivity maximum is at comparatively high conversions, is less marked and decreases less markedly with increasing conversion.

Multimetal oxides M of the type A are preferentially suitable in the process according to the invention for charging the catalyst bed I, while multimetal oxides M of the type B are preferentially suitable for charging the catalyst bed II.

In general, type A multimetal oxides M include the multimetal oxides of the stoichiometry A $$Mo_1V_aTe_bNb_cX^1_dO_n \quad (A)$$

where
$X^1$=Ag, Ga, Pd and/or Sm,
a=from 0.01 to 1,
b=from >0 to 1,
c=from >0 to 1,
d=from >0 to 0.5 and
n=a number which is determined by the valency and frequency of the elements in A other than oxygen.

The type B multimetal oxides generally include multimetal oxides of the stoichiometry B $$Mo_1V_aTe_bNb_cX^2_eO_x \quad (B)$$

where
$X^2$=Ni, Co, Bi, Cu, Fe, Mn, Nd, Pb, Re and/or Pt,
a=from 0.01 to 1,
b=from >0 to 1,
c=from >0 to 1,
e=from $\geq$0 to 0.5 and
x=a number which is determined by the valency and frequency of the elements in B other than oxygen.

Both in the case of the stoichiometry A and in the case of the stoichiometry B, irrespective of the preferred ranges for the other stoichiometric coefficients of the two stoichiometries A, B the stoichiometric coefficient a is preferably from 0.05 to 0.6, more preferably from 0.1 to 0.6 or 0.5.

Irrespective of the preferred ranges for the other stoichiometric coefficients of the two stoichiometries A, B, the stoichiometric coefficient b is preferably from 0.01 to 1 and more preferably from 0.01 to 0.05 or from 0.1 to 0.5 or 0.4.

The stoichiometric coefficient c of the multimetal oxides M of the stoichiometry A, B to be used advantageously in accordance with the invention, irrespective of the preferred ranges for the other stoichiometric coefficients of the stoichiometries A, B is from 0.01 to 1 and more preferably from 0.01 or 0.05 or 0.1 to 0.5 or 0.4. A range for the stoichiometric coefficient c which is very particularly preferred in accordance with the invention and can be combined irrespective of the preferred ranges for the other stoichiometric coefficients of the stoichiometries A, B is the range from 0.05 to 0.2.

Preference is given in accordance with the invention to the stoichiometric coefficient d or e of the stoichiometries A, B, irrespective of the preferred ranges for the other stoichiometric coefficients, being from 0.00005 or 0.0005 to 0.5, more preferably from 0.001 to 0.5, frequently from 0.002 to 0.3 and often from 0.005 or 0.01 to 0.1.

Particularly favorable multimetal oxides M of the stoichiometry A or B which are to be used in accordance with the invention are those whose stoichiometric coefficients a, b, c and d or e are simultaneously within the following framework:

a=from 0.05 to 0.6;
b=from 0.01 to 1 (or from 0.01 to 0.5);
c=from 0.01 to 1 (or from 0.01 to 0.5); and
d, e=from 0.0005 to 0.5 (or from 0.001 to 0.3).

Very particularly favorable multimetal oxides M of the type A, B to be used in accordance with the invention are those whose stoichiometric coefficients a, b, c and d or e are simultaneously within the following framework:

a=from 0.1 to 0.6;
b=from 0.1 to 0.5;
c=from 0.05 or 0.1 to 0.5; and
d, e=from 0.001 to 0.5 or from 0.002 to 0.3 or from 0.005 to 0.1.

The aforementioned correlations are substantially also retained when the element Te in the stoichiometries A, B is replaced by the element Sb or by the element Bi or by at least two of the elements Sb, Te and Bi.

In addition, all of the aforementioned correlations are also substantially retained when the element Nb in the stoichiometries A, B is replaced by one of the elements Ce, Ti, W or Ta or by a mixture of elements from the group consisting of Nb, Ti, W, Ta and Ce.

It is common knowledge that catalytically active multimetal oxides M may occur in different crystalline phases (cf., for example, DE-A 10246119 and DE-A 10254279).

One of the possible crystalline phases, known as the k phase (having hexagonal structure, frequently also known as M2 phase), is characterized by an X-ray diffractogram which has particularly intense reflections at the 2Θ peak locations 22.1±0.5°, 28.2±0.5°, 36.2, ±0.5°, 45.2±0.5° and 50.0±0.3°.

A second specific crystal structure (orthorhombic structure) in which the relevant multimetal oxides M may occur is generally referred to as i phase (frequently also as M1 phase). One feature of its X-ray diffractogram is that it has particularly intense reflections at the 2Θ peak locations 22.2±0.5°, 27.3±0.5°, 28.2±0.5°, but, in contrast to the k phase, has no reflection at the 2Θ peak location 50.0±0.3° (cf. DE-A 10119933 and DE-A 10118814).

The customary preparative processes of the relevant multimetal oxides M (for example the preparative processes of WO 0206199, EP-A 1192987, EP-A 529853 and EP-A 603836) do not normally provide either pure k phase or pure i phase, but rather mixed crystal structures which are an intertwined mixture of k and i phase in which the k phase fraction normally dominates.

A measure of the i phase fraction in these mixed crystal structures is the intensity ratio $$R=P_i/(P_i+P_k)$$

where $P_i$ is the intensity of the reflection i at 2Θ=27.3±0.5° and $P_k$ is the intensity of the reflection k at 2Θ=28.2±0.5° in the accompanying X-ray diffractogram.

Particularly high i phase fractions are present when 0.55 or 0.65$\leq$R$\leq$0.85. Preference is given in accordance with the invention to high i phase fractions in the multimetal oxides M to be used in accordance with the invention, both for those of the stoichiometry A and for those of the stoichiometry B. For both stoichiometries A, B pure i phase is advantageous in accordance with the invention.

Preferably in accordance with the invention, for both stoichiometries A, B therefore, 0.65$\leq$R$\leq$0.85 or 0.67$\leq$R$\leq$0.75 and, very particularly preferably, R=from 0.69 to 0.75 or R=from 0.71 to 0.74 or 0.73, or R=0.72.

In addition to the reflections h, i and k, the X-ray diffractogram of the catalytically active multimetal oxides M to be used in accordance with the invention (irrespective of their stoichiometry) generally also contains further reflections whose peak locations are at the following reflection angles (2Θ):

9.0±0.4° (l),
6.7±0.4° (o) and
7.9±0.4° (p).

It is also favorable in accordance with the invention when the X-ray diffractogram additionally contains a reflection whose peak location is at the reflection angle (2Θ)=45.2±0.4° (q).

Frequently, the X-ray diffractogram of multimetal oxides M to be used in accordance with the invention (irrespective of their stoichiometry) also contains the reflections 29.2±0.4° (m) and 35.4±0.4° (n) (peak locations).

When the intensity 100 is assigned to the reflection h, it is favorable in accordance with the invention when the reflections i, l, m, n, o, p, q in the same intensity scale have the following intensities:

i: from 5 to 95, frequently from 5 to 80, in some cases from 10 to 60;
l: from 1 to 30;
m: from 1 to 40;
n: from 1 to 40
o: from 1 to 30;
p: from 1 to 30 and
q: from 5 to 60.

When the X-ray diffractogram of the multimetal oxides M to be used in accordance with the invention (irrespective of their stoichiometry) contains the aforementioned additional reflections, their half-height width is generally ≦1°.

The specific surface area of multimetal oxides M to be used in accordance with the invention (irrespective of their stoichiometry) is in many cases from 1 to 40 $m^2/g$, advantageously 10, 11 or 12 to 40 $m^2/g$ and frequently from 15 or 20 to 40 or 30 $m^2/g$ (determined by the BET method, nitrogen).

Preference is given in accordance with the invention (irrespective of their stoichiometry), as already stated, to using those multimetal oxides M whose X-ray diffractogram has no reflection having the peak location 2Θ=50.0±0.3°.

All data relating to an X-ray diffractogram in this document relate to an X-ray diffractogram generated using Cu-Kα radiation as the X-ray radiation (Siemens Theta-Theta D-5000 diffractometer, tube voltage: 40 kV, tube current: 40 mA, aperture V20 (variable), collimator V20 (variable), secondary monochromator aperture (0.1 mm), detector aperture (0.6 mm), measuring interval (2Θ): 0.02°, measuring time per step: 2.4 s, detector: scintillation counting tube; definition of the intensity of a reflection in the X-ray diffractogram relates in this document to the definition laid down in DE-A 19835247, DE-A 10122027, and also in DE-A 10051419 and DE-A 10046672; the same applies to the definition of the half-height width).

The preparation processes described in the prior art (cf., for example, DE-A 19835247, EP-A 529853, EP-A 603836, EP-A 608838, EP-A 895809, EP-A 962253, EP-A 1080784, EP-A 1090684, EP-A 1123738, EP-A 1192987, EP-A 1192986, EP-A 1192982, EP-A 1192983 and EP-A 1192988) for multimetal oxides M generally provide mixed crystal systems composed of i phase and k phase. In these processes, a very intimate, preferably finely divided, dry mixture is generated from suitable sources of the elemental constituents of the multimetal oxide M and thermally treated at temperatures of from 350 to 700° C. or from 400 to 650° C. or from 400 to 600° C. The thermal treatment may in principle be effected either under an oxidizing, a reducing or under an inert atmosphere. A useful oxidizing atmosphere is, for example, air, air enriched with molecular oxygen or air depleted in oxygen. However, preference is given to carrying out the thermal treatment under an inert atmosphere, i.e., for example, under molecular nitrogen and/or noble gas. Typically, the thermal treatment is effected at atmospheric pressure (1 atm). It will be appreciated that the thermal treatment may also be effected under reduced pressure or under elevated pressure.

When the thermal treatment is effected under gaseous atmosphere, it may either be stationary or flow. It preferably flows. Overall, the thermal treatment may take up to 24 h or more.

Preference is given to effecting the thermal treatment initially under an oxidizing (oxygen-containing) atmosphere (for example under air) at a temperature of from 150 to 400° C. or from 250 to 350° C. (=predecomposition step). Afterward, the thermal treatment is appropriately continued under inert gas at temperatures of from 350 to 700° C. or from 400 to 650° C. or from 450 to 600° C. It will be appreciated that the thermal treatment may also be effected in such a way that the catalyst precursor composition, before its thermal treatment, is initially (optionally after pulverization) tableted (optionally with the addition of from 0.5 to 2% by weight of finely divided graphite), then thermally treated and subsequently spalled again.

The intimate mixing of the starting compounds may be effected in dry or in wet form.

When it is effected in wet form, the starting compounds are appropriately used as finely divided powder and, after the mixing and any compaction, subjected to calcination (thermal treatment).

However, preference is given to effecting the intimate mixing in wet form. Typically, the starting compounds are mixed together in the form of an aqueous solution (optionally with the use of complexing agents; cf., for example, DE-A 10145958) and/or suspension. Subsequently, the aqueous composition is dried and calcined after the drying. Appropriately, the aqueous composition is an aqueous solution or an aqueous suspension. Preference is given to effecting the drying process directly after the preparation of the aqueous mixture (especially in the case of an aqueous solution; cf., for example, JP-A 7-315842) and by spray drying (the exit temperatures are generally from 100 to 150° C.; the spray drying may be carried out in cocurrent or in countercurrent), which results in a particularly intimate dry mixture, in particular when the aqueous composition to be spray-dried is an aqueous solution or suspension.

However, it may also be dried by concentrating by evaporation under reduced pressure, by freeze-drying or by conventional concentration by evaporation.

When the above-described preparation method of i/k phase mixed crystal multimetal oxide compositions is carried out, useful sources for the elemental constituents are all of those which are capable of forming oxides and/or hydroxides on heating (optionally under air). It will be appreciated that such starting compounds may also already partly or exclusively be oxides and/or hydroxides of the elemental constituents. In other words, useful starting compounds are especially all of those mentioned in EP-A 1254707, EP-A 1254709 and EP-A 1192987.

Suitable sources for the element Mo are, for example, molybdenum oxides such as molybdenum trioxide, molybdates such as ammonium heptamolybdate tetrahydrate and molybdenum halides such as molybdenum chloride.

Suitable starting compounds for the element V are, for example, vanadium oxysulfate hydrate, vanadyl acetylacetonate, vanadates such as ammonium metavanadate, vanadium oxides such as vanadium pentoxide ($V_2O_5$), vanadium halides such as vanadium tetrachloride ($VCl_4$) and vanadium oxyhalides such as $VOCl_3$. The vanadium starting compounds used may also be those which contain the vanadium in the +4 oxidation state.

Suitable sources for the element tellurium are tellurium oxides such as tellurium dioxide, metallic tellurium, tellurium halides such as $TeCl_2$, but also telluric acids such as orthotelluric acid $H_6TeO_6$.

Advantageous antimony starting compounds are antimony halides such as $SbCl_3$, antimony oxides such as antimony trioxide ($Sb_2O_3$), antimony trioxide pretreated with $H_2O_2$, antimony acids such as $HSb(OH)_6$, but also antimony oxide salts such as antimony oxide sulfate $(SbO)_2SO_4$ and antimony acetate.

Suitable niobium sources are, for example, niobium oxides such as niobium pentoxide ($Nb_2O_5$), niobium oxide halides such as $NbOCl_3$, niobium halides such as $NbCl_5$, but also complexes of niobium and alcohols (e.g. ethanol, n-propanol), organic carboxylic acids and/or dicarboxylic acids, for example oxalates and alkoxides. It will be appreciated that useful niobium sources are also the Nb-containing solutions used in EP-A 895 809.

With regard to all other possible elements (in particular Pb, Ni, Cu, Co, Bi and Pd), suitable starting compounds are in particular their halides, nitrates, formates, oxalates, acetates, carbonates and/or hydroxides. Suitable starting compounds are in many cases also their oxo compounds, for example tungstates or acids derived from them. The starting compounds used are frequently also ammonium salts.

Useful starting compounds are also polyanions of the Anderson type, as described, for example, in Polyhedron Vol. 6, No. 2, pp. 213–218, 1987. A further suitable literature source for polyanions of the Anderson type is Kinetics and Catalysis, Vol. 40, No. 3, 1999, pp 401 to 404.

Other polyanions suitable as starting compounds are, for example, those of the Dawson or Keggin type. Preference is given to using those starting compounds which are converted to their oxides at elevated temperatures, either in the presence or with the exclusion of oxygen, in some cases with the release of gaseous compounds.

In the i/k phase mixed crystal multimetal oxides M obtained as described (pure i phase multimetal oxides M are obtained coincidentally at best by the procedure described), the fraction of i phase may be increased or isolated by washing out the k phase to the desired extent using suitable liquids. Preference is given to calcining once again after the washing, as described in EP-A 1254709. The calcination conditions are generally those which were also recommended for preparing the multimetal oxide M to be washed. The predecomposition may, however, be dispensed with.

Useful such washing liquids are, for example, organic acids and aqueous solutions of organic acids (e.g. oxalic acid, formic acid, acetic acid, citric acid and tartaric acid), inorganic acids (e.g. nitric acid), aqueous solutions of inorganic acids (e.g. aqueous telluric acid or aqueous nitric acid), alcohols and aqueous hydrogen peroxide solutions. In addition, JP-A 7-232071 also discloses a process for preparing i phase-rich multimetal oxides M. Likewise suitable is the washing process of EP-A 1254707 and of EP-A 1254706.

An increased fraction of i phase (and in favorable cases substantially pure i phase) is generally attained in the preparation of multimetal oxides M when they are prepared by a hydrothermal route, as described, for example, in DE-A 10029338, DE-A 10254278 and JP-A 2000-143244. In this case too, washing may be effected subsequently and recalcination may be effected in accordance with EP-A 1254709.

However, active multimetal oxides M of the stoichiometry A, B where d or e>0 which are to be used advantageously in accordance with the invention may also be prepared by initially generating a multimetal oxide M' which differs from a multimetal oxide M only in that d=0.

Such a preferably finely divided multimetal oxide M' may then be saturated with solutions (for example aqueous) of elements $X^1$, $X^2$ (for example by spraying), subsequently dried (preferably at temperatures $\leq 100°$ C.) and then, as already described for the multimetal oxide M', calcined (preferably in an inert gas stream; preference is given here to dispensing with predecomposition under air). The use of aqueous nitrate and/or halide solutions of elements $X^1$, $X^2$ and/or the use of aqueous solutions in which the elements $X^1$, $X^2$ are complexed with organic compounds (for example acetates or acetylacetonates) is particularly advantageous for this preparative variant.

The active multimetal oxides M to be used in accordance with the invention and obtainable as described, in particular those of the stoichiometry A, B, may be used in the process according to the invention as such [for example as a powder or after tableting the powder (frequently with the addition of from 0.5 to 2% by weight of finely divided graphite) and subsequent spalling to give spall comminuted] or may be used as catalysts for the process according to the invention shaped to shaped bodies. The individual catalyst bed may be a fixed bed, a moving bed or a fluidized bed.

The shaping to shaped bodies may be effected, for example, by applying to a support body, as described in DE-A 10118814, or WO 02/83615, or DE-A 10051419. The procedure may also correspond to that of DE-A 4442346.

The support bodies to be used for the active multimetal oxides M to be used in the process according to the invention are preferably chemically inert. In other words, they substantially do not intervene in the course of the heterogeneously catalyzed gas phase partial oxidation according to the invention which is catalyzed by the multimetal oxides M to be used in accordance with the invention, in particular those of the stoichiometries A, B.

According to the invention, useful materials for the support bodies are in particular aluminum oxide, silicon dioxide, silicates such as clay, kaolin, steatite (preferably having a low water-soluble alkali content and also preferably from Ceramtec in Germany, for example steatite C220), pumice, aluminum silicate and magnesium silicate, silicon carbide, zirconium dioxide and thorium dioxide.

The surface of the support body may be either smooth or rough. Advantageously, the surface of the support body is rough, since increased surface roughness generally results in increased adhesion of the applied active composition coating.

Frequently, the surface roughness $R_z$ of the support body is in the range from 5 to 200 μm, often in the range from 20 to 100 μm (determined according to DIN 4768 sheet 1 using a "Hommel tester for DIN-ISO surface parameters" from Hommelwerke, Germany).

In addition, the support material may be porous or nonporous. Appropriately, the support material is nonporous (total volume of the pores based on the volume of the support body $\leq 1\%$ by volume).

The thickness of the active oxide composition coating on the coated catalysts according to the invention is typically from 10 to 1000 μm. However, it may also be from 50 to 700 μm, from 100 to 600 μm or from 150 to 400 μm. Possible coating thicknesses are also from 10 to 500 μm, from 100 to 500 μm or from 150 to 300 μm.

In principle, any geometries of the support bodies are useful for the process according to the invention. Their longest dimension is generally from 1 to 10 mm. However, preference is given to using spheres or cylinders, in particular hollow cylinders, as support bodies. Favorable diameters for support spheres are from 1.5 to 5 mm. When cylinders are used as support bodies, their length is preferably from 2 to 10 mm and their external diameter is preferably from 4 to 10 mm. In the case of rings, the wall thickness is additionally typically from 1 to 4 mm. Annular support bodies which are suitable in accordance with the invention may also have a length of from 3 to 6 mm, an external diameter of from 4 to 8 mm and a wall thickness of from 1 to 2 mm. However, a support ring geometry of 7 mm×3 mm×4 mm or of 5 mm×3 mm×2 mm (external diameter×length×internal diameter) is also possible.

Coated catalysts to be used in accordance with the invention may be prepared in the simplest manner, for example, in such a way that multimetal oxides M to be used in accordance with the invention, in particular those of the general stoichiometry A, B, are preformed, they are converted to finely divided form and finally applied to the surface of the support body with the aid of a liquid binder. To this end, the surface of the support body is, in the simplest manner, moistened with the liquid binder and a layer of the active composition is attached to the moistened surface by contacting with finely divided active oxide composition, for example those of the general stoichiometry A, B. Finally, the coated support body is dried. It will be appreciated that the procedure may be repeated periodically to achieve increased layer thickness. In this case, the coated parent body becomes the new "support body", etc. On completion of coating, calcination may be effected once again under the conditions already specified (preferably again under inert gas).

The fineness of the catalytically active multimetal oxide to be applied to the surface of the support body, for example that of the general stoichiometry A, B, is of course adapted to the particular coating thickness. Suitable for the coating thickness range of from 100 to 500 μm are, for example, those active composition powders of which at least 50% of the total number of powder particles pass through a sieve of mesh width from 1 to 20 μm and whose numerical fraction of particles having a longest dimension of above 50 mm is less than 10%. In general, the distribution of the longest dimensions of the powder particles, as a result of the preparation, corresponds to a Gaussian distribution. Frequently, the particle size distribution is as follows:

and $\leq 90°$; the inclination angle is the angle of the central axis of the rotary vessel relative to the horizontal) rotating vessel (for example rotary pan or coating drum). The rotating vessel conducts the, for example, spherical or cylindrical support bodies under two metering devices arranged successively in a certain separation. The first of the two metering devices appropriately corresponds to a nozzle (for example an atomizer nozzle operated with compressed air), which sprays the support bodies rolling in the rotary pan with the liquid binder and moistens them in a controlled manner. The second metering device is outside the atomization cone of the sprayed liquid binder and serves to feed the finely divided oxidic active composition (for example via an agitated channel or a powder screw). The support spheres which have been moistened in a controlled manner take up the active composition powder supplied, which is compressed by the rolling motion to a continuous coating on the outer surface of the, for example, cylindrical or spherical, support body.

If required, the support body basically coated in this way, in the course of the subsequent rotation, again passes through the spray nozzles, and is moistened in a controlled manner, in order, in the course of the further motion, to be able to take up a further layer of finely divided oxidic active composition, etc. (intermediate drying is generally not necessary). Finely divided oxidic active composition and liquid binder are generally supplied continuously and simultaneously.

The liquid binder may be removed on completion of coating, for example by the action of hot gases such as $N_2$ or air. Remarkably, the coating process described brings about fully satisfactory adhesion of the subsequent layers both to each other and to the base layer on the surface of the support body.

It is essential for the above-described coating method that the moistening of the surface of the support body to be coated is carried out in a controlled manner. In short, this means that the support surface is appropriately moistened in such a way that, although it has adsorbed liquid binder, no liquid phase as such visibly appears on the support surface. When the support body surface is too moist, the finely divided catalytically active oxide composition agglomerates to separate agglomerates, instead of to the surface. Detailed information on this subject can be found in DE-A 2909671 and in DE-A 10051419.

The aforementioned final removal of the liquid binder used can be carried out in a controlled manner, for example by evaporation and/or sublimation. In the simplest case, this may be effected by the action of hot gases at appropriate

| D (μm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

D = diameter of the particle,
x = the percentage of the particles whose diameter is $\geq D$; and
y = the percentage of the particles whose diameter is $<D$.

For a performance of the coating process described on the industrial scale, it is recommended, for example, to employ the process principle disclosed in DE-A 2909671, and also in DE-A 10051419. In other words, the support bodies to be coated are initially charged in a preferably inclined (the inclination angle is generally $\geq 0°$ and $\leq 90°$, usually $\geq 30°$ temperature (frequently from 50 to 300° C., frequently 150° C.). However, the action of hot gases may also be used only to bring about predrying. The final drying may then be effected, for example, in a drying oven of a known type (for example belt dryer) or in the reactor. The action temperature should not be above the calcination temperature employed to prepare the oxidic active composition. However, it will be appreciated that the drying may also be carried out exclusively in a drying oven.

The binder used for the coating process, irrespective of the type and the geometry of the support body, may be: water, monohydric alcohols such as ethanol, methanol, propanol and butanol, polyhydric alcohols such as ethylene glycol, 1,4-butanediol, 1,6-hexanediol or glycerol, mono- or polybasic organic carboxylic acids such as propionic acid, oxalic acid, malonic acid, glutaric acid or maleic acid, amino alcohols such as ethanolamine or diethanolamine, or else mono- or polyhydric organic amides such as formamide. Suitable binders are also solutions consisting of from 20 to 90% by weight of water and from 10 to 80% by weight of an organic compound dissolved in water whose boiling point or sublimation temperature at atmospheric pressure (1 atm) is >100° C., preferably >150° C. Advantageously, the organic compound is selected from the above listing of possible organic binders. The organic fraction of the aforementioned aqueous binder solutions is preferably from 10 to 50% by weight and more preferably from 20 to 30% by weight. Useful organic components are also monosaccharides and oligosaccharides such as glucose, fructose, sucrose or lactose, and also polyethylene oxides and polyacrylates.

It is significant that coated catalysts which are suitable in accordance with the invention can be prepared not only by applying the finished, finely ground active oxide compositions M, for example of the general stoichiometry A, B, to the moistened support body surface.

Rather, instead of the active multimetal oxides M, a finely divided precursor composition thereof may also be applied to the moistened support surface (employing the same coating process and binder) and the calcination carried out after drying the coated support body (support bodies may also be impregnated with a precursor solution, subsequently dried and then calcined). Finally, the k phase different to the i phase may be washed out. Subsequently, calcination may be repeated in the manner described.

Such a finely divided precursor composition may be, for example, that composition which is obtainable by initially generating a very intimate, preferably finely divided dry mixture from the sources of the elemental constituents of the desired active multimetal oxide M to be used in accordance with the invention, for example that of the general stoichiometry A, B, (for example by spray drying an aqueous suspension or solution of the sources) and thermally treating this finely divided dry mixture (optionally after tableting with the addition of 0.5 to 2% by weight of finely divided graphite) at a temperature of from 150 to 350° C., preferably from 250 to 350° C., under an oxidizing (oxygen-containing) atmosphere (for example under air) (a few hours) and finally, if required, subjecting it to grinding.

After the coating of the support bodies with the precursor composition, calcination is then effected, preferably under an inert gas atmosphere (all other atmospheres are also possible), at temperatures of from 360 to 700° C. or from 400 to 650° C. or from 450 to 600° C.

It will be appreciated that active multimetal oxides M which can be used in accordance with the invention, for example those of the general stoichiometry A, B, may also be shaped by extrusion and/or tableting, either of finely divided multimetal oxide M or of finely divided precursor composition of an active multimetal oxide M (if necessary, the phases other than the i phase may finally be washed out, optionally including a recalcination).

Useful geometries are spheres, solid cylinders and hollow cylinders (rings). The longest dimension of the aforementioned geometries is generally from 1 to 10 mm. In the case of cylinders, their length is preferably from 2 to 10 mm and their external diameter is preferably from 4 to 10 mm. In the case of rings, the wall thickness is additionally typically from 1 to 4 mm. Annular unsupported catalysts suitable according to the invention may also have a length of from 3 to 6 mm, an external diameter of from 4 to 8 mm and a wall thickness of from 1 to 2 mm. However, an unsupported catalyst ring geometry of 7 mm×3 mm×4 mm or of 5 mm×3 mm×2 mm (external diameter×length×internal diameter) is also possible.

The geometries of the multimetal oxide M catalysts to be used for the process according to the invention, in particular those of the general stoichiometry A, B, may of course also be all of those of DE-A 10101695.

In this document, the definition of the intensity of a reflection in the X-ray diffractogram relates, as already stated, to the definition laid down in DE-A 19835247, and also in DE-A 10051419 and DE-A 10046672.

In other words, if $A^1$ denotes the peak location of a reflection 1 and $B^1$, in the line of the X-ray diffractogram viewed along the intensity axis at right angles to the 2Θ axis, denotes the next pronounced minimum (minima having reflection shoulders are not taken into account) to the left of the peak location $A^1$ and $B^2$ is correspondingly the next pronounced minimum to the right of the peak location $A^1$ and $C^1$ is the point at which a straight line drawn from the peak location $A^1$ at right angles to the 2Θ axis cuts a straight line joining the points $B^1$ and $B^2$, the intensity of the reflection 1 is the length of the straight line section $A^1C^1$ which then extends from the peak location $A^1$ to the point $C^1$. The expression minimum in this context means a point at which the slope of a tangent to the curve in a base region of the reflection 1 changes from a negative value to a positive value, or a point at which the slope tends to zero, using the coordinates of the 2Θ axis and of the intensity axis for the determination of the slope.

In this document, the half-height width is correspondingly the length of the straight line section between the two intersection points $H^1$ and $H^2$ when a line is drawn parallel to the 2Θ axis in the middle of the straight line section $A^1C^1$, $H^1$, $H^2$ meaning in each case the first point at which these parallel lines cut the line as defined above of the X-ray diffractogram to the left and right of $A^1$.

An exemplary execution of the determination of half-height width and intensity is also shown by FIG. 6 in DE-A 10046672.

It will be appreciated that the multimetal oxides M to be used in accordance with the invention, in particular those of the general stoichiometry A, B, may also be used as catalytic active compositions diluted with finely divided, for example colloidal, materials such as silicon dioxide, titanium dioxide, aluminum oxide, zirconium oxide, niobium oxide.

The dilution composition ratio may be up to 9 (diluent):1 (active composition). In other words, possible diluent composition ratios are, for example, 6 (diluent):1 (active composition) and 3 (diluent):1 (active composition). The diluent may be incorporated before and/or after the calcination, generally even before the drying. It is normally effected before the shaping. When the incorporation is effected before the drying or before the calcination, the diluent has to be selected in such a way that it is substantially preserved in the fluid medium or in the calcination. This is the case, for example, for diluent oxides calcined at appropriately high temperatures.

It is possible to differentiate into catalysts which are more suitable for a fixed catalyst bed I or more suitable for a fixed catalyst bed II not only via the stoichiometry of the multimetal oxide M forming its active composition. Rather, such a differentiation may be brought about for the same stoichiometry, for example, via the preparation process.

When the maximum calcination temperature is employed, for example, in the range from 470 to 570° C., a catalyst results which is more suitable for a catalyst bed I. In contrast, when the maximum calcination temperature employed is in the range from >570° C. to 670° C., a catalyst results which is more suitable for a catalyst bed II.

Washing of the multimetal oxide M as described above by means of suitable washing liquids (for example organic acids, inorganic acids, hydrogen peroxide solutions, etc.) may likewise bring about shifting of the multimetal oxide M from "more suitable for a catalyst bed II" to "more suitable for a catalyst bed I".

In addition, the working pressure or the GHSV selected in both catalyst beds I, II may be different. Preference is given in accordance with the invention to selecting an elevated (for example relative to the catalyst beds I) working pressure in the catalyst beds II.

Quite generally, suitable catalysts for the process according to the invention are therefore those whose multimetal oxide M satisfies the following general stoichiometry C $$Mo_1V_aM^1_bM^2_cM^3_dO_m \tag{C}$$

where
$M^1$=at least one of the elements from the group consisting of Te and Sb;
$M^2$=at least one of the elements from the group consisting of Nb, Ti, W, Ta and Ce;
$M^3$=at least one of the elements from the group consisting of Pb, Ni, Co, Bi, Pd, Ca, Mg, Fe, Mn, Ag, Pt, Cu, Au, Ga, Zn, Sn, In, Re, Ir, Sm, Sc, Y, Pr, Nd and Tb;
a=from 0.01 to 1,
b=from >0 to 1,
c=from >0 to 1,
d=from $\geq$0 to 0.5 (preferably from >0 to 0.5) and
m=a number which is determined by the valency and frequency of the elements in (C) other than oxygen.

With regard to the stoichiometric coefficients a, b, c and d of the multimetal oxides C, the same applies as was stated for the multimetal oxide A. The same applies with regard to the X-ray diffractogram of the multimetal oxides C.

Both the catalyst bed I and the catalyst bed II in the process according to the invention may be a fluidized bed, moving bed or a fixed bed. The catalyst bed I and the catalyst bed II may be disposed either in one reactor or in different reactors connected in series. In other words, the reactor unit of the process according to the invention may consist of only one reactor or of a plurality of reactors, for example connected in series. The different aforementioned bed types may also be employed in combination.

In the simplest case, both the catalyst bed I and the catalyst bed II are each a fixed bed which are both disposed in a single reactor, preferably in a tube bundle reactor.

When the catalyst beds are disposed in different reactors, the reaction gas mixture may optionally be supplemented by inert gas and/or oxygen at the transition from one to the other reactor.

Especially when the catalyst beds are disposed in a single reactor, the reaction gas mixture is generally retained at the transition from the catalyst bed I into the catalyst bed II.

It will be appreciated that, in the process according to the invention, target product present in the product gas mixture leaving the catalyst charge may be removed therefrom and remaining residual product gas mixture may be recycled as cycle gas and recycled back into the reaction unit as a constituent of the starting reaction gas mixture, as recommended, for example, in DE-A 10316465 and in EP-A 1193240.

In addition, the catalyst beds I, II in the process according to the invention may be kept at substantially uniform or at different temperature (in this document, temperature of a catalyst bed refers to the temperature of the catalyst bed when the process according to the invention is performed, but in the theoretical absence of a chemical reaction (i.e. without the influence of the heat of reaction)).

Preference is given to setting the temperature of the catalyst bed I to the value at which, for the case that the overall catalyst charge of the same reactor unit were to consist only of catalyst bed of type I, the selectivity $S^I$ of (meth)acrylic acid formation would attain its maximum value $S^I_{max}$ with otherwise identical conditions of the gas phase partial oxidation.

In the process according to the invention, preference is given to setting the temperature of the catalyst bed II to the value for which, in the case that the overall catalyst charge of the same reactor unit were to consist only of the catalyst bed of the type II, the selectivity $S^{II}$ of (meth)acrylic acid formation attains its maximum value $S^{II}_{max}$ with otherwise identical conditions of the gas phase partial oxidation.

The size of the catalyst bed I (for example the length of the appropriate catalyst bed) is advantageously selected in accordance with the invention in such a way that, under the selected process conditions, the conversion of the saturated hydrocarbon precursor compound existing at the end of the catalyst bed I does not deviate by more than 20 or 10 mol %, preferably not more than 5 mol %, from that conversion value to which $S^I_{max}$ corresponds, this conversion value simultaneously forming the basis for the aforementioned percentage deviation.

When the catalyst bed I and the catalyst bed II are disposed in different reactors, the setting of-different bed temperatures is trivial. However, even when they are disposed in one and the same reactor, a different catalyst bed temperature is possible in a simple manner, for example, by employing a multizone reactor as described for the case of tube bundle reactors by DE-A 19910506, DE-A 10313213, DE-A 10313208 and EP-A 1106598. A uniform temperature for the catalyst bed I and the catalyst bed II can be realized, for example, in a simple manner in a one-zone multiple catalyst tube fixed bed reactor, as described by DE-A 4431957, EP-A 700714 and EP-A 700893.

It is essential to the invention that the active composition of the catalysts of the catalyst bed I or II may in each case consist of only one or else more than one multimetal oxide M. The resulting catalysts may also vary along a catalyst bed I (or II). In addition, the catalysts of the catalyst bed I or II may also be diluted with inert shaped diluent bodies in the particular catalyst bed. Useful materials for such inert shaped diluent bodies include all of those of which the support bodies for the coated catalysts may consist. The geometry of the particular shaped diluent bodies preferably corresponds to those of the catalysts to be diluted. However, it may also be different from their geometry.

In addition, the fraction of the inert shaped diluent bodies may also decrease or increase continuously, abruptly or stepwise in the flow direction of the reaction gas mixture within the individual catalyst beds I, II. Between catalyst bed I and catalyst bed II may be disposed, if required in the process according to the invention, pure inert shaped diluent bodies.

According to the invention, the temperature of the catalyst beds I, II is advantageously from 200 to 550° C., frequently from 230 to 480° C. or from 300 to 440° C.

Useful sources for the molecular oxygen required in the process according to the invention may be, for example, air, oxygen-enriched or oxygen-depleted air or pure oxygen.

Otherwise, the starting reaction gas mixture may comprise, in addition to the saturated hydrocarbon precursor compound and molecular oxygen and also any steam, inert diluent gases (this refers quite generally to those gases of which, in the process according to the invention (based on single pass) more than 95 mol %, preferably more than 98 mol %, remain chemically unchanged), for example $N_2$ and $CO_2$. Frequently, the starting reaction gas mixture also comprises CO, for example in the case of the cycle gas method.

In other words, the starting reaction gas mixture with which the entire catalyst charge is to be charged at pressures of generally from 1 to 10 bar, or from 2 to 5 bar (reduced pressure may in principle also be employed) may have, for example, the following contents:
from 1 to 15 or 20, preferably from 1 to 10 or 7, % by volume of precursor compound (for example propane),
from 0 or 5 to 25 or 50% by volume of steam and
from 10 to 80% by volume of air.

However, it may also have the following contents:
from 2 to 10% by volume of precursor compound (for example propane),
from 5 to 20% by volume of steam,
from 60 to 85% by volume of nitrogen, and
from 5 to 15% by volume of oxygen.

According to the invention, the starting reaction gas mixture used may also be a starting reaction gas mixture as described in the documents EP-A 608838, WO 0029106, JP-A 10-36311, DE-A 10316465, EP-A 1192987, EP-A 1193240 and DE-A 10338529.

Multimetal oxide active compositions deactivated in the process according to the invention may be reactivated as described in DE-A 10338529.

When the saturated hydrocarbon used in the process according to the invention is crude propane, its composition is preferably as described in DE-A 10246119, or DE-A 10118814, or WO 02/83615.

The start-up of a fresh catalyst charge may be carried out as described in DE-A 10122027.

Based on the propane and/or isobutane present in the starting reaction gas mixture, the conversion of propane and/or isobutane in the process according to the invention, based on single pass of the reaction gas mixture through the overall catalyst charge (=the sum of all individual catalyst beds arranged in succession), will generally be from 10 or 20 to 90 or 70 mol %, frequently from 30 to 60 mol % and in many cases from 40 to 60 mol % or from 45 to 55 mol %.

The selectivity of target product formation ((meth)acrylic acid) will typically be from 40 to 98 or from 45 to 90 mol %, in many cases from 50 to 80 mol %, often from 60 to 80 mol %.

The target product removal and any cycle gas control may be as described in DE-A 10316465.

The hourly space velocity on the overall catalyst charge (not including pure inert zones) of propane and/or isobutane may be from 10 to 1000 l (STP)/l (catalyst charge)/h or from 20 to 800 l (STP)/l/h, or from 50 to 600 l (STP)/l/h, or from 100 to 500 l (STP)/l/h, or from 150 to 300 l (STP)/l/h.

The hourly space velocity on the overall catalyst charge (not including pure inert zones) of starting reaction gas mixture may be from 10 to 10 000 l (STP)/l/h, or from 300 to 6000 l (STP)/l/h or from 600 to 3000 l (STP)/l/h. The average residence time in the catalyst charge may be from 0.01 to 10 s, or from 0.1 to 10 s, or from 2 to 6 s. The advantage of the process according to the invention is an increased maximum yield of (meth)acrylic acid based on single pass of the reaction gas mixture through the catalyst charge of the reactor unit.

EXAMPLES AND COMPARATIVE EXAMPLES

A) Preparation of a coated catalyst A having a multimetal oxide active composition A which has a stoichiometry A of the following composition:

$Mo_1V_{0.28}Te_{0.13}Nb_{0.10}Ga_{0.019}O_n$.

79.65 g of ammonium metavanadate (78.55% by weight of $V_2O_5$, from G.f.E. Nuremberg) were dissolved at 80° C. in 3000 ml of water (three-neck flask with stirrer, thermometer and reflux condenser, heater). This gave a yellowish clear solution. This solution was cooled to 60° C. and then, while maintaining the 60° C., in the sequence specified, 122.34 g of telluric acid (99% by weight of $H_6TeO_6$, from Aldrich) and 400.00 g of ammonium heptamolybdate (82.52% by weight of $MoO_3$, from Starck/Goslar) were successively stirred into the solution. The resulting deep red solution was cooled to 30° C. and then, while maintaining the 30° C. admixed with a solution of 33.40 g of gallium(III) nitrate hydrate (19.17% by weight of Ga, from Aldrich) in 40 g of water (dissolution at 25° C.). A solution A was obtained in this way and was at 30° C.

Separately therefrom, 81.94 g of ammonium niobium oxalate (20.8% by weight of Nb, from Starck/Goslar) were dissolved at 60° C. in 500 ml of water in a beaker to obtain a solution B. Solution B was cooled to 30° C. and combined at this temperature with the solution A at the same temperature by adding solution B to solution A. The addition was effected constantly over a period of 5 min. This gave an orange-colored suspension.

This suspension was subsequently spray-dried in a Niro spray dryer (Niro A/S atomizer spray dryer, Mobile Minor, centrifugal atomizer from Niro, Denmark) within 1.5 h. The reservoir temperature was 30° C. The gas inlet temperature $T^{in}$ was 320° C., the gas outlet temperature $T^{out}$ was 110° C. The resulting spray powder was likewise orange-colored.

The sprayed material was admixed with 1% by weight of finely divided graphite (sieve analysis: min. 50% by weight ≦24 μm, max. 10% by weight >24 μm and ≦48 μm, max. 5% by weight >48 μm, BET surface area: from 6 to 13 $m^2$/g).

The resulting mixture was compacted (compressed) to hollow cylinders (rings) of geometry 16 mm×25 mm×8 mm (external diameter×height×internal diameter) in such a way that the resulting side crushing strengths of the rings were approx. 10 N.

Two portions each of 100 g of the rings were each heated initially linearly from 25° C. to 275° C. in a rotary sphere furnace according to FIG. 1 of DE-A 10122027 under an air stream of 100 l (STP)/h within 27.5 min., and this temperature and the air stream were subsequently maintained for 1 h. Immediately thereafter, the air stream was replaced by a nitrogen stream of 100 l (STP)/h and heating was effected linearly from 275° C. to 600° C. within 32.5 min. This temperature and the nitrogen stream were then maintained over 2 h. Subsequently, the entire rotary sphere furnace was cooled to 25° C. while maintaining the nitrogen stream.

Black rings of the composition $Mo_{1.0}V_{0.30}Te_{0.21}Nb_{0.08}Ga_{0.04}O_n$ (empirical stoichiometry: $Mo_{1.0}V_{0.03}Te_{0.23}Nb_{0.08}Ga_{0.40}O_n$) were obtained.

The rings were subsequently ground in a Retsch mill (ZM 100 centrifugal mill from Retsch, Germany) (particle size $\leq 0.12$ mm). 100 g of this powder were stirred under reflux in 1000 ml of a 10% by weight aqueous $HNO_3$ solution at 70° C. over 7 h, and the solid was filtered out of the resulting slurry and washed with water to free it of nitrate. The filtercake was dried in a muffle furnace at 110° C. under air overnight.

The resulting active composition A had the composition $Mo_1V_{0.28}Te_{0.13}Nb_{0.1}Ga_{0.019}O_n$.

The accompanying X-ray diffractogram reveals pure i phase.

38 g of the resulting active composition powder were applied to 150 g of spherical support bodies having a diameter of from 2.2 to 3.2 mm ($R_z$=45 µm, support material=steatite from Ceramtec, Germany, total pore volume of the support $\leq 1\%$ by volume based on the total support volume). To this end, the support was initially charged into a coating drum having a capacity of 2 l (inclination angle of the drum central axis relative to the horizontal=30°). The drum was rotated at 25 revolutions per minute. An atomizer nozzle operated at 300 l (STP)/h of compressed air was used to spray approx. 25 ml of a mixture of glycerol and water (glycerol:water weight ratio=1:3) onto the support for 60 min. The nozzle was installed in such a way that the spray cone wetted the support bodies conveyed within the drum to the uppermost point of the inclined drum by means of carrier plates, in the upper half of the roll-off section. The finely divided active composition powder was introduced into the drum via a powder screw, and the point of powder addition was within the roll-off section or below the spray cone. The periodic repetition of wetting and powder replenishment resulted in the initially coated support body itself becoming the support body in the subsequent period.

On completion of coating, the coated support body was dried in a muffle furnace under air at 150° C. for 16 h. This resulted in a coated catalyst A having an active composition fraction of 20% by weight.

B) Preparation of a coated catalyst B having a multimetal oxide active composition B which has a stoichiometry B of the following composition:

$$Mo_1V_{0.29}Te_{0.14}Nb_{0.13}Ni_{0.007}O_x.$$

87.61 g of ammonium metavanadate (78.55% by weight of $V_2O_5$, from G.f.E. Nuremberg) were dissolved with stirring at 80° C. in 3040 ml of water (three-neck flask with stirrer, thermometer, reflux condenser and heater). This gave a yellowish clear solution. This solution was cooled to 60° C. and then, while maintaining the 60° C., in the sequence specified, 117.03 g of telluric acid (99% by weight of $H_6TeO_6$, from Aldrich) and 400.00 g of ammonium heptamolybdate (82.52% by weight of $MoO_3$, from Starck/Goslar) were successively stirred into the solution. The resulting deep red solution was cooled to 30° C. and then, while maintaining the 30° C., admixed with 25.60 g of an aqueous solution of 5.60 g of nickel(II) nitrate hexahydrate (98% by weight, from Fluka) in 20 g of water (dissolution at 25° C.). A solution A was obtained in this way and was at 30° C.

Separately therefrom, 112.67 g of ammonium niobium oxalate (20.8% by weight of Nb, from Starck/Goslar) were dissolved at 60° C. in 500 ml of water in a beaker to obtain a solution B. Solution B was cooled to 30° C. and combined at this temperature with the solution A at the same temperature by adding solution B to solution A. The addition was effected constantly over a period of 5 min. This gave an orange-colored suspension.

This suspension was subsequently spray-dried in a Niro spray dryer (Niro A/S atomizer spray dryer, Mobile Minor, centrifugal atomizer from Niro, Denmark) within 1.5 h. The reservoir temperature was 30° C. The gas inlet temperature $T^{in}$ was 320° C., the gas outlet temperature was $T^{out}$ was 110° C. The resulting spray powder was likewise orange-colored.

The sprayed material was admixed with 1% by weight of finely divided graphite (sieve analysis: min. 50% by weight $\leq 24$ µm, max. 10% by weight >24 µm and $\leq 48$ µm, max. 5% by weight >48 µm, BET surface area: from 6 to 13 m²/g).

The resulting mixture was compacted (compressed) to hollow cylinders (rings) of geometry 16 mm×25 mm×8 mm (external diameter×height×internal diameter) in such a way that the resulting side crushing strengths of the rings were approx. 10 N.

Two portions each of 100 g of the rings were each heated initially linearly from 25° C. to 275° C. in a rotary sphere furnace according to FIG. 1 of DE-A 10122027 under an air stream of 50 l (STP)/h within 27.5 min., and this temperature and the air stream were subsequently maintained for 1 h. Immediately thereafter, the air stream was replaced by a nitrogen stream of 50 l (STP)/h and heating was effected linearly from 275° C. to 600° C. within 32.5 min. This temperature and the nitrogen stream were then maintained over 2 h. Subsequently, the entire rotary sphere furnace was cooled to 25° C. while maintaining the nitrogen stream.

Black rings of the composition 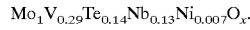 $Mo_{1.0}V_{0.33}Te_{0.19}Nb_{0.11}Ni_{0.01}O_x$ (empirical stoichiometry: $Mo_{1.0}V_{0.33}Te_{0.22}Nb_{0.11}Ni_{0.01}O_x$) were obtained.

The rings were subsequently ground in a Retsch mill (ZM 100 centrifugal mill from Retsch, Germany) (particle size $\leq 0.12$ mm).

100 g of this powder were stirred under reflux in 1000 ml of a 10% by weight aqueous $HNO_3$ solution at 70° C. over 7 h, and the solid was filtered out of the resulting slurry and washed with water to free it of nitrate. The filtercake was dried in a muffle furnace at 110° C. under air overnight. The resulting active composition B had the composition $Mo_1V_{0.29}Te_{0.14}Nb_{0.13}Ni_{0.007}O_x$.

The accompanying X-ray diffractogram revealed pure i phase.

38 g of the resulting active composition powder were applied to 150 g of spherical support bodies having a diameter of from 2.2 to 3.2 mm ($R_z$=45 µm, support material=steatite from Ceramtec, Germany, total pore volume of the support $\leq 1\%$ by volume based on the total support volume). To this end, the support was initially charged into a coating drum having a capacity of 2 l (inclination angle of the drum central axis relative to the horizontal=30°). The drum was rotated at 25 revolutions per minute. An atomizer nozzle operated at 300 l (STP)/h of compressed air was used to spray approx. 25 ml of a mixture of glycerol and water (glycerol:water weight ratio=1:3) onto the support for 60 min. The nozzle was installed in such a way that the spray cone wetted the support bodies conveyed within the drum to the uppermost point of the inclined drum by means of carrier plates, in the upper half of the roll-off section. The finely divided active composition powder was introduced into the drum via a powder screw, and the point of powder addition was within the roll-off section or below the spray cone. The periodic repetition of wetting and powder replenishment resulted in the initially coated support body itself becoming the support body in the subsequent period.

On completion of coating, the coated support body was dried in a muffle furnace under air at 150° C. for 16 h. This resulted in a coated catalyst B having an active composition fraction of 20% by weight.

C) Process for preparing acrylic acid by heterogeneously catalyzed gas phase partial oxidation of propane

1. COMPARATIVE EXAMPLES 35.0 g of the particular coated catalyst A, B are each installed into a single-tube reactor (tube length: 140 cm, internal diameter: 8.5 mm, external diameter: 60 mm, V2A steel, catalyst bed length: 53.0 cm, additionally for heating the starting reaction gas mixture, a 30 cm-long preliminary bed of steatite spheres from Ceramtec (C 220, diameter from 2.2 to 3.2 mm), and the reaction tube is also finally filled with the same steatite spheres downstream of the catalyst zone), which is heated by electrical heating mats. The particular coated catalyst is installed at a mat temperature of 350° C. under air.

Afterward, the particular reaction tube is started up, while maintaining the mat temperature of 350° C. for 24 h, with a starting reaction gas mixture (charge gas mixture) which has the following composition:
  3.3% by volume of propane,
  10% by volume of $O_2$,
  40% by volume of $N_2$ and
  46.7% by volume of $H_2O$.

The residence time selected (based on the catalyst bed volume) is 2.4 s, the reaction tube inlet pressure is 2 bar absolute, the GHSV is 1500 $h^{-1}$ (based on the charge gas mixture).

The (propane) conversion C/selectivity S (of acrylic acid formation) dependence is then determined by appropriately increasing the heating mat temperatures (to 410° C.) while maintaining the other boundary conditions.

The table which follows shows the results as a function of the coated catalyst used. In addition, it shows the yield of acrylic acid (molar amount of acrylic acid forming in 1 h).

TABLE 1

|                  | C (mol %) | S (mol %) | Y (mol/h) |
|------------------|-----------|-----------|-----------|
| Coated catalyst A | 10        | 91        | 0.006     |
|                  | 20        | 78        | 0.010     |
|                  | 30        | 63        | 0.012     |
|                  | 40        | 44        | 0.011     |
|                  | 50        | 18        | 0.007     |
| Coated catalyst B | 10        | 45        | 0.003     |
|                  | 20        | 65        | 0.008     |
|                  | 30        | 71        | 0.014     |
|                  | 40        | 71        | 0.018     |
|                  | 50        | 71        | 0.023     |
|                  | 60        | 68        | 0.026     |
|                  | 70        | 62        | 0.028     |
|                  | 80        | 52        | 0.027     |

2. EXAMPLES

The comparative examples are repeated as described. However, the catalyst bed length (charge) is structured as follows:

Example 1 in the flow direction of the reaction gas mixture, first to 10% of the bed length, coated catalyst A (bed I), then to 90% of the bed length, coated catalyst B (bed II).

Example 2 in the flow direction of the reaction gas mixture, first to 20% of the bed length, coated catalyst A (bed I), then to 80% of the bed length, coated catalyst B (bed II).

The following table 2 shows the results.

TABLE 2

|           | C (mol %) | S (mol %) | Y (mol/h) |
|-----------|-----------|-----------|-----------|
| Example 1 | 10        | 46        | 0.003     |
|           | 20        | 68        | 0.009     |
|           | 30        | 73        | 0.014     |
|           | 40        | 74        | 0.019     |
|           | 50        | 74        | 0.024     |
|           | 60        | 74        | 0.028     |
|           | 70        | 68        | 0.031     |
|           | 80        | 58        | 0.030     |
| Example 2 | 10        | 48        | 0.003     |
|           | 20        | 68        | 0.009     |
|           | 30        | 75        | 0.014     |
|           | 40        | 76        | 0.020     |
|           | 50        | 75        | 0.025     |
|           | 60        | 73        | 0.028     |
|           | 70        | 70        | 0.032     |
|           | 80        | 62        | 0.032     |

When the reaction tube inlet pressure is increased to 3 bar absolute, the results are as follows:

TABLE 3

|           | C (mol %) | S (mol %) | Y (mol/h) |
|-----------|-----------|-----------|-----------|
| Example 1 | 60        | 73        | 0.028     |
|           | 70        | 72        | 0.032     |
|           | 80        | 69        | 0.035     |
| Example 2 | 60        | 75        | 0.030     |
|           | 70        | 73        | 0.033     |
|           | 80        | 69        | 0.036     |

The U.S. Provisional Application 60/504,959, filed on Sep. 23, 2003, is incorporated into the present application by reference.

With regard to the abovementioned teachings, numerous alterations and deviations from the present invention are possible. It may therefore be assumed that the invention, within the scope of the appended claims, may be performed differently than specifically described herein.

We claim:

1. A process for preparing (meth)acrylic acid by heterogeneously catalyzed gas phase partial oxidation of at least one saturated hydrocarbon precursor compound at elevated temperature, by conducting a starting reaction gas mixture which comprises the at least one saturated hydrocarbon precursor compound, molecular oxygen and at least one inert gas and has a starting pressure P through a catalyst charge which is disposed in a reactor unit and whose catalysts are such that their active composition is at least one multimetal oxide M which contains the elements Mo and V, at least one of the elements Te, Sb and Bi, and at least one of the elements from the group consisting of Nb, Ta, W, Ce and Ti, and whose X-ray diffractogram is an X-ray diffractogram which has reflections h, i and k whose peak locations are at the reflections (2Θ)) of 22.2±0.5° (h), 27.3±0.5° (i) and 28.2±0.5° (k), the reflection h being the most intense within the X-ray diffractogram and also having a half-height width of at most 0.5° and the half-height width of the reflection i and of the reflection k each being ≦1°,
wherein
the catalyst charge in its entirety consists of two catalyst beds I, II which comprise different catalysts and are spatially successive in the flow direction of the reaction gas mixture, the catalyst bed I being such that if the overall catalyst charge of the same reactor unit were to consist only of catalyst bed of the type I, the selectivity $S^I$ of (meth)acrylic acid formation with otherwise identical conditions of the gas phase partial oxidation would, depending on the conversion, be increased by increasing the reaction temperature, of the saturated hydrocarbon precursor compound based on single pass of the reaction gas mixture through the reactor unit, pass through a maximum value $S^I_{max}$, and the catalyst bed II being such that if the overall catalyst charge of the same reactor unit were to consist only of catalyst bed of the type II, the selectivity $S^{II}$ of (meth)acrylic acid formation with otherwise identical conditions of the gas phase partial oxidation would, depending on the conversion, be increased by increasing the reaction temperature, of the saturated hydrocarbon precursor compound based on single pass of the reaction gas mixture through the reactor unit, pass through a maximum value $S^{II}_{max}$, with the proviso that the value $S^I_{max}$ is at a lower conversion of the saturated hydrocarbon precursor compound than the value $S^{II}_{max}$ and, with increasing conversion of the saturated hydrocarbon precursor compound, $S^I < S^{II}$, whereas $S^I_{max} > S^{II}_{max}$.

2. A process as claimed in claim 1, wherein the active composition of the catalysts of the fixed catalyst bed I is at least one multimetal oxide M of the stoichiometry A $$Mo_1V_aTe_bNb_cX^1_dO_n \qquad (A)$$

where
X$^1$=Ag, Ga, Pd and/or Sm,
a=from 0.01 to 1,
b=from >0 to 1,
c=from >0 to 1,
d=from >0 to 0.5 and
n=a number which is determined by the valency and frequency of the elements in A other than oxygen.

3. A process as claimed in claim 2, wherein the stoichiometric coefficient a of the stoichiometry A is from 0.05 to 0.6.

4. A process as claimed in claim 2, wherein the stoichiometric coefficient b of the stoichiometry A is from 0.01 to 1.

5. A process as claimed in claim 2, wherein the stoichiometric coefficient c of the stoichiometry A is from 0.01 to 1.

6. A process as claimed in claim 2, wherein the stoichiometric coefficient d of the stoichiometry A is from 0.00005 to 0.5.

7. A process as claimed in claim 2, wherein the stoichiometric coefficients of the stoichiometry A are within the following framework:
a=from 0.05 to 0.6;
b=from 0.01 to 1;
c=from 0.01 to 1; and
d=from 0.00005 to 0.5.

8. A process as claimed in claim 2, wherein the element Te in the stoichiometry A is replaced by the element Sb or by the element Bi.

9. A process as claimed in claim 2, wherein the element Te in the stoichiometry A is replaced by at least two of the elements Sb, Te and Bi.

10. A process as claimed in claim 1, wherein the active composition of the catalysts of the fixed catalyst bed II is at least one multimetal oxide M of the stoichiometry B $$Mo_1V_aTe_bNb_cX^2_eO_x \qquad (B)$$

where
X$^2$=Ni, Co, Bi, Cu, Fe, Mn, Nd, Pb, Re and/or Pt,
a=from 0.01 to 1,
b=from >0 to 1,
c=from >0 to 1,
e=from $\geq$0 to 0.5 and
x=a number which is determined by the valency and frequency of the elements in B other than oxygen.

11. A process as claimed in claim 10, wherein the stoichiometric coefficient a of the stoichiometry B is from 0.05 to 0.6.

12. A process as claimed in claim 10, wherein the stoichiometric coefficient b of the stoichiometry B is from 0.01 to 1.

13. A process as claimed in claim 10, wherein the stoichiometric coefficient c of the stoichiometry B is from 0.01 to 1.

14. A process as claimed in claim 10, wherein the stoichiometric coefficient e of the stoichiometry B is from 0.00005 to 0.5.

15. A process as claimed in claim 10, wherein the stoichiometric coefficients of the stoichiometry B are within the following framework:
a=from 0.05 to 0.6;
b=from 0.01 to 1;
c=from 0.01 to 1; and
d=from 0.00005 to 0.5.

16. A process as claimed in claim 10, wherein the element Te in the stoichiometry B is replaced by the element Sb or by the element Bi.

17. A process as claimed in claim 10, wherein the element Te in the stoichiometry B is replaced by at least two of the elements Te, Sb and Bi.

18. A process as claimed in claim 1, wherein, for the intensity ratio $$R=P_i/(P_i+P_k)$$

where $P_i$ is the intensity of the reflection i at 2$\Theta$=27.3$\pm$0.5° and $P_k$ is the intensity of the reflection k at 2$\Theta$=28.2$\pm$0.5° in the X-ray diffractogram of the at least one multimetal oxide M, 0.55$\leq$R$\leq$0.85.

19. A process as claimed in claim 1, wherein the X-ray diffractogram of the at least one multimetal oxide M has no reflection having the peak location 2$\Theta$=50.0$\pm$0.3°.

20. A process as claimed in claim 1, wherein the catalysts of the catalyst beds I, II are coated catalysts.

21. A process as claimed in claim 1, wherein both the catalyst bed I and the catalyst bed II are a fixed bed.

* * * * *